United States Patent [19]
Tjoeng et al.

[11] Patent Number: 5,354,738
[45] Date of Patent: Oct. 11, 1994

[54] PLATELET AGGREGATION INHIBITORS

[75] Inventors: Foe S. Tjoeng, Manchester, Mo.; Jeffery A. Zablocki, Skokie, Ill.

[73] Assignees: G. D. Searle & Co., Chicago, Ill.; The Monsanto Company, St. Louis, Mo.

[21] Appl. No.: 940,569

[22] Filed: Sep. 4, 1992

[51] Int. Cl.$^5$ .................. C07D 209/18; A61K 37/02; A61K 31/405; C07C 273/18
[52] U.S. Cl. .................................... 514/19; 548/496; 548/110; 562/439; 560/34; 546/300; 546/14; 549/55; 549/467; 549/493
[58] Field of Search .............. 548/495, 496, 110; 514/419, 19; 560/34; 562/439; 549/55, 467, 493; 546/300

[56] References Cited

U.S. PATENT DOCUMENTS

| | | | |
|---|---|---|---|
| 4,515,803 | 5/1985 | Henning et al. | 514/338 |
| 4,849,408 | 7/1989 | Sommermeyer et al. | 514/18 |
| 5,292,935 | 3/1994 | Lalezari et al. | 560/34 X |

FOREIGN PATENT DOCUMENTS

| | | | |
|---|---|---|---|
| 90101404.3 | 1/1990 | European Pat. Off. | |
| 91103462.7 | 3/1991 | European Pat. Off. | C07K 5/06 |
| 513675 | 11/1992 | European Pat. Off. | C07K 5/06 |
| WO92/15607 | 9/1992 | PCT Int'l Appl. | C07K 5/06 |

OTHER PUBLICATIONS

Bovy et al., U.S. Ser. No. 07/847,260 dated Mar. 6, 1992.
Zablocki et al., U.S. Ser. No. 07/908,128 dated Jul. 1, 1992.

*Primary Examiner*—David B. Springer
*Attorney, Agent, or Firm*—Cynthia S. Kovacevic; Roger A. Williams

[57] ABSTRACT

This invention relates to compounds having the following formula

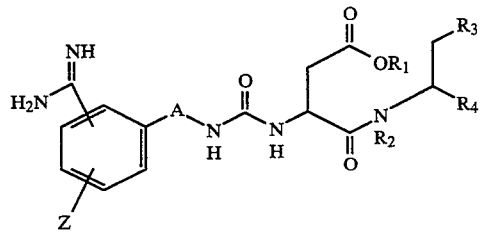

or a pharmaceutically acceptable salt thereof which are useful in the inhibition of platelet aggregation, to pharmaceutical compositions including the compounds, and to a method of inhibiting platelet aggregation in mammals by administering such compounds and compositions.

18 Claims, No Drawings

PLATELET AGGREGATION INHIBITORS

FIELD OF THE INVENTION

The present invention relates to pharmaceutical agents and compounds which inhibit platelet aggregation in mammals.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

European Patent Application 445,796 discloses platelet aggregation inhibitors which contain peptide linkages, namely N-[N-[4-(p-amidinobenzamido)butyryl]L-α-aspartyl]valine compounds. The compounds inhibit cell-cell adhesion and the binding of adhesive proteins to platelets.

European Patent Application 372,486 discloses N-acyl beta amino acid derivatives which are useful as cell adhesion inhibitors and are especially useful for inhibiting platelet aggregation.

European Patent Application 381,033 discloses amidino or guanidinoaryl substituted alkanoic acid derivatives which inhibit protein to receptor binding and are useful for the treatment of thrombosis and cardiac infarction.

SUMMARY OF THE INVENTION

The present invention relates to a class of compounds represented by the formula:

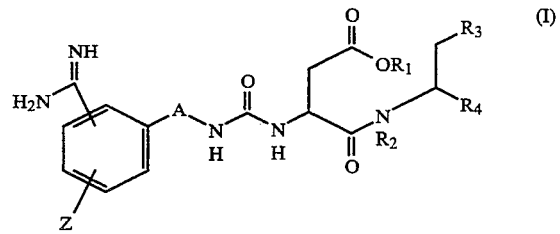

or a pharmaceutically acceptable salt thereof
wherein Z is selected from the group consisting of H, halogen, hydroxy, alkoxy of one to six carbon atoms and alkyl of one to six carbon atoms;
wherein A is selected from the group consisting of alkyl of one to six carbon atoms, alkenyl of two to six carbon atoms and alkynyl of two to six carbon atoms;
wherein $R_1$ is selected from the group consisting of H, alkyl of one to six carbon atoms, aralkyl and alkanoyloxyalkyl;
wherein $R_2$ is selected from the group consisting of H, alkyl of one to six carbon atoms, and aralkyl optionally substituted on the aryl by hydroxy or methoxy;
wherein $R_3$ is selected from the group consisting of alkyl, indolyl, pyridyl, benzothiophenyl, phenyl benzofuranyl and furanyl optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino;
wherein $R_4$ is selected from the group consisting of H, —COOR$_5$ and —(CH$_2$)$_m$COOR$_5$;
wherein m is an integer from 1 to 6; and
wherein $R_5$ is selected from the group consisting of H, alkyl of one to six carbon atoms and aralkyl.

It is another object of the invention to provide pharmaceutical compositions comprising compounds of the formula I. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

The present invention relates to a class of compounds represented by the formula I, described above.

A preferred embodiment of the present invention is a compound of the formula I wherein:
Z is hydrogen;
A is alkyl of one to six carbon atoms;
wherein $R_1$ is selected from the group consisting of H and alkyl of one to six carbon atoms; and
$R_2$ is selected from the group consisting of hydrogen, alkyl of one to six carbon atoms, and aralkyl optionally substituted on the aryl ring by hydroxy or methoxy;
wherein $R_3$ is indolyl optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino;

wherein R⁴ is selected from the group consisting of H,
—COOR₅ and —(CH₂)ₘCOOR₅;
wherein m is an integer from 1 to 6; and
wherein R₅ is selected from the group consisting of H,
alkyl of one to six carbon atoms and aralkyl.
Another preferred embodiment of the present invention
is a compound of the formula I wherein:
Z is hydrogen;
A is alkyl of one to six carbon atoms;
R₁ is selected from the group consisting of hydrogen
and alkyl of one to six carbon atoms; and
R₂ is selected from the group consisting of H, alkyl of
one to six carbon atoms, and aralkyl optionally substituted on the aryl ring by hydroxy or methoxy;
wherein R³ is pyridyl optionally substituted by a radical
selected from the group consisting of halogen, alkyl
of one to six carbon atoms, alkoxy of one to six carbon atoms, carboxyl derivatives, nitro, cyano, azido,
ureido, ureylene, alkoxycarbonyloxy, hydroxyl, alkylamino, alkoxycarbonyl, trialkylsilyl, alkoxyimino,
alkylsulfonyl, phenylsulfonyl and amino;
wherein R⁴ is selected from the group consisting of H,
—COOR₅ and —(CH₂)ₘCOOR₅;
wherein m is an integer from 1 to 6; and wherein R₅ is
selected from the group consisting of H, alkyl of one
to six carbon atoms and aralkyl.
Still another preferred embodiment is a compound of
the formula I wherein:
Z is hydrogen;
A is alkyl of one to six carbon atoms;
R₁ is selected from the group consisting of hydrogen
and alkyl of one to six carbon atoms; and
R₂ is selected from the group consisting of H, alkyl of
one to six carbon atoms, and aralkyl optionally substituted on the aryl ring with hydroxy or methoxy;
wherein R³ is phenyl optionally substituted by a radical
selected from the group consisting of halogen, alkyl
of one to six carbon atoms, alkoxy of one to six carbon atoms, carboxyl derivatives, nitro, cyano, azido,
ureido, ureylene, alkoxycarbonyloxy, hydroxyl, alkylamino, alkoxycarbonyl, trialkylsilyl, alkoxyimino,
alkylsulfonyl, phenylsulfonyl and amino;
wherein R⁴ is selected from the group consisting of H,
—COOR₅ and —(CH₂)ₘCOOR₅;
wherein m is an integer from 1 to 6; and
wherein R₅ is selected from the group consisting of H,
alkyl of one to six carbon atoms and aralkyl.
Exemplifying these embodiments are the following
compounds:
N-[N-[[[4-[4-(aminoiminomethyl)phenyl]butyl]amino]-carbonyl]-L-α-aspartyl]-L-phenylalanine, diethyl ester
N-[N-[[[4-[4-(aminoiminomethyl)phenyl]butyl]amino]-carbonyl]-L-α-aspartyl]-L-phenylalanine.
N-[N-[[[4-[4-(aminoiminomethyl)phenyl]butyl]amino]-carbonyl]-L-α-aspartyl]-L-tryptophane As used herein, the term "alkyl" refers to a straight chain or branched chain hydrocarbon radical having from 1 to 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein, the term "alkoxy" includes straight or branched chain lower alkyl ether radicals wherein the term alkyl is as defined above. Examples of such groups are methoxy, ethoxy, n-propoxy, n-butoxy, isobutoxy, t-butoxy, sec-butoxy, isopropoxy and the like.

As used herein the term "halogen" refers to chloro (Cl), fluoro (F), bromo (Br) or iodo (I).

As used herein the term "alkenyl" refers to unsaturated acyclic hydrocarbons containing at least one double bond and 2 to 6 carbon atoms. Examples of such groups are ethenyl, propenyl, butenyl, isobutenyl, pentenyl, hexenyl and the like.

As used herein the term "alkynyl" refers to acyclic hydrocarbons containing one or more triple bonds and 2 to 6 carbon atoms. Examples of such groups are ethynyl, propynyl, butynyl, pentynyl, hexynyl and the like.

As used herein the term "heteroaryl wherein the heteroatom is N" refers to a radical composed of at least one unsaturated ring wherein one of the carbon atoms is replaced by nitrogen. Examples of such groups are pyridyl, quinolinyl, and the like.

As used herein the term "aralkyl" refers to a radical wherein an aryl group, such as phenyl, naphthyl or pyridyl is attached to an alkyl radical as defined above. Examples of such radicals include benzyl, phenylpropyl, pyridylmethyl and the like.

As used herein the term "aryl" refers to an organic radical derived from an aromatic hydrocarbon by the removal of one atom, such as, phenyl is formed from the removal of one atom from benzene and the like.

As used herein the term "carboxyl derivatives" refer to a radical of the general formula

wherein
R is hydrogen or alkyl as defined above.

As used herein the term "alkoxycarbonyl" refers to a radical of the formula

wherein R is an alkyl group as defined above.

As used herein "alkylamino" refers to a radical of the formula —NHR or —NRR wherein R is an alkyl group as defined above.

The compounds herein as shown in Formula I can exist in various isomeric forms and all such isomeric forms are intended to be included, as well as, pharmaceutically acceptable salts of such compounds and isomers.

In the structures and formulas herein, a bond drawn across a bond of a ring can be to any available atom on the ring.

The term "pharmaceutically acceptable salt" refers to a salt prepared by conventional means. Examples of pharmaceutically acceptable salts include the hydrochloride, hydrobromide, hydroiodide, sulfate, phosphate, acetate, propionate, lactate, maleate, malate, succinate, and tartrate salts. (See Berge et al., *J Pharm. Sci.*, 66(1), 1–19 (1977) for additional examples of pharmaceutically acceptable salts.)

This invention also relates to a method of inhibiting platelet aggregation and more specifically, a method of treatment involving the administration of compounds of Formula I to achieve such inhibition.

The platelet aggregation inhibitors of the present invention are useful in the prevention of re-occlusion of an artery following re-canalization procedures such as post-fibrinolytic therapy, thrombolytic therapy, angioplasty and coronary bypass surgery. Other contemplated uses are prevention of recurrent myocardial infarct, unstable angina, peripheral artery disease, cerebral ischemia and shunt procedures.

For the inhibition of platelet aggregation, compounds of the present invention may be administered orally, parenterally, or by inhalation spray, rectally, or topically in dosage unit formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 150 mg per kilogram of body weight per day are useful in the treatment of the above-indicated conditions. The pharmacologically active compounds of this invention can be processed in accordance with conventional methods of galenic pharmacy to produce medicinal agents for administration to patients, e.g., mammals including humans.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The novel platelet aggregation inhibitors of the present invention can be prepared by methods analogous to solution phase peptide synthesis [see: The Peptides: Analysis, Synthesis, Biology (E. Gross and J. Meienhofer, eds.), Vol. 1–5, Academic Press, New York)] combined with standard synthetic method. The general synthetic sequence is outlined in Scheme A. The cyano group is converted to the amidine via the imidate which is formed by treating the benzonitrile with anhydrous hydrochloric acid in ethanol. Treatment of the imidate with ammonium chloride affords the amidine as the salt (HCl). Selective hydrolysis of the ester in the presence of the amidine can be carried out using lithium hydroxide in aqueous methanol. The final compounds for biological testing were obtained by purification by reverse phase high pressure liquid chromatography [High Performance Liquid Chromatography Protein and Peptide Chemistry (F. Lottspeich, A. Henscher, K. P. Hupe, eds.) Walter DeGruyter, New York, 1981].

The benzonitrile urea derivative of Scheme A can be prepared from the corresponding acid derivative using a Curtius rearrangement as outlined in Scheme B. The intermediate isocyanate can be prepared in a three step process using trimethylsilylazide [H. R. Kricheldorf, Chem. Ber., Vol. 105, 3958–3965 (1972)] followed by aqueous hydrolysis to the amine. The amine is converted to the isocyanate by treatment with triphosghene [H. Eckert and B. Forsten, *Angew. Chem. Int. Ed. Engl.* 894–895 (1987)] and subsequent reaction with the dipeptide mimetic affords the benzonitrile urea of Scheme A.

Alternatively, the benzonitrile urea is obtained directly from the corresponding acid by treatment with diphenylphosphorylazide [S. Yamada, K. Ninomiya and T. Shioiri *Tetrahedron Lett.* 2343 (1973); P. A. S. Smith Org. React. Vol. 3, 337 (1946); J. H. Saunders, R. J. Slocombe, *Chem. Rev.,* V. 43, 203 (1948)] followed by trapping the intermediate isocyanate with the dipeptide mimetic.

The benzonitrile acid of Scheme B where A=alkenyl, alkynyl, or alkyl having 2 to 4 carbon atoms can be prepared in the following manner (Scheme C): The halobenzonitrile (Z=H) is coupled to an omega alkynoic (Scheme C-Method 1) or alkenoic acid (Scheme C-Method 2) using a palladium(0) based coupling reaction ["Heck Reaction"—Palladium Reagents in Organic Syntheses (Richard F. Heck), Academic Press, New York, 1985].

The preferred conditions for the palladium coupling reaction differed for the alkynoic acid and the alkenoic acid coupling components. When A=alkynyl having 2 to 4 carbon atoms, the preferred conditions for the palladium coupling reaction utilized tetrakis(triphenylphosphine)-palladium(0) as catalyst and piperidine as the solvent [Scheme C-Method 1, for related conditions see: H. A. Dieck and F. R. Heck *J. Organometallic Chem.* 259–263(1975)]. When A=alkenyl having 2 to 4 carbon atoms, the preferred conditions for the alkenoic acid coupling component utilized the phase transfer conditions of Jeffery and Larock [Scheme C-Method 2, T. Jeffery *J. Chem. Soc. Chem. Commun.* 1287–89(1984); R. C. Larock *Tetrahedron Lett.* 2603–2606 (1989)]. These conditions [phase transfer agent-tetrabutylammonium salt, catalyst-palladium(II) acetate, base-potassium acetate, solvent-dimethyl formamide] are extremely mild conditions which afforded a good yield of coupled olefin. Compounds where A=alkyl were obtained through a selective reduction of the double bond by catalytic reduction over palladium on calcium carbonate.

The required omega alkenoic acids are either commercially available or can be synthesized by oxidation of the omega alkenols [E. J. Corey and G. Schmidt *Tetrahedron Lett.* 399 (1979)]. The required omega alkynoic acids are either commercially available or can be synthesized from the omega haloalkanoic acids and lithium acetylide [W. J. DeJarlais, E. A. Emken *Synthetic Commun.* 653 (1980); J. Cossy, J. P. Pete *Tetrahedron Lett.* 573 (1986)].

An alternative method for the preparation of the (cyanophenyl)alkenoic acid unit (A=alkenyl) can be employed using a standard Wittig reaction [B. E. Maryanoff, A. B. Reitz *Chem Rev.* 863–927 (1989)] with cyanobenzaldehyde and an omega substituted (carboxyalkyl)triphenylphosphonium bromide as the two reaction components (Scheme C- Method 3) [for related conditions see: *J. Am. Chem. Soc.* 397 (1970); Ibid 6831 and 7185 (1973)].

The substituents, Z=halogen, alkyl, hydroxy, or alkoxy, can be introduced where A=alkyl at the benzonitrile stage (e.g. compound 4, Scheme F) using bromine, iodine, or chlorine to halogenate the ring (Scheme D). The alkyl group can be introduced by low temperature lithium halogen exchange followed by quenching with the appropriate aldehyde [see: W. E. Parham, C. K. Bradsher *Acct. Chem. Res.* 300 (1982)]. The resultant alcohol can be converted to Z=alkyl by hydrogenolysis [Reductions in Organic Chemistry (M. Hudlicky, ed.), John Wiley & Sons, New York, 1984] as shown in Scheme D.

The substituents, Z=hydroxy or alkoxy, can be introduced by low temperature lithium halogen exchange followed by quenching with the electrophilic bis(trimethylsilyl)peroxide [(TMSO)2-Scheme D) M. Taddei and A. Ricci *Synthesis* 633–635 (1986)] which affords the silyl ether. The silyl ether can be converted to the Z=OH by treatment with hydrochloric acid [M. Taddei and A. Ricci ibid]. The Z=OR can be formed by treating the derivative where Z=OH with weak base (K2CO3) and an appropriate alkyl halide [R8-Hal, 2 equivalents, see: C. F. H. Allen and J. W. Gates, Jr. *Organic Syntheses Coll. Vol.* 3 140 (1955)] which will form the ester as well. The ester can be selectively cleaved in the presence of the ether with one equivalent of sodium hydroxide (Scheme D).

Compounds, where R2=alkyl, phenyl or phenylalkyl can be prepared by condensation of the appropriate secondary amine with aspartic acid which can be purchased or readily synthesized through a Michael reaction [Advanced Organic Chemistry (J. March, ed.), John Wiley & Sons, New York, 1985] of a primary amine and tert-butyl acrylate or reductive amination [Reductions in Organic Chemistry (M. Hudlicky, ed.), John Wiley & Sons, New York, 1984] processes using the appropriate primary amine and aldehyde.

The amino acid containing R2, R3, and R4 is either commercially available or readily synthesized from the available aldehyde as illustrated in Scheme E. Homologation of the aldehyde using a Wittig reaction [B. E. Marynoff and A. B. Reitz, *Chem. Rev.,* 863–927 (1989)] followed by a Strecker amino acid synthesis [Principles of Organic Synthesis (R. O. C. Norman, ed.), John Wiley & Sons, New York, 1978] affords the amino acid as illustrated in Scheme E.

Compounds where R4=alkyl carboxyl can be prepared by homologation of commercially available amino acids using the Arndt-Eistert reaction [Meir and Zeller *Angw. Chem. Int. Ed. Eng.* 32–43 (1975); M. Rodriguez et al *Tetrahedrron Lett.* 5153 (1990); W. J. Greenlee *J. Med. Chem.* 434 (1985) and references therein] or utilizing other known syntheses of homologated amino acids [e.g. phenylalanine is homologated through the addition of a malonate anion to an activated aziridine obtained from phenylalanine—Tseng, C. C., Terashima, S. and Yamada, S. I. *Chem. Pharm. Bull.* 29–40 (1977)].

A specific synthesis of antiplatelet agent 10 N-[N-[[4-[4-(aminoiminomethyl)phenyl]butyl]amino]carbonyl]-L-α-aspartyl]-L-phenylalanine. is shown in Scheme F. The compound numbers used in Scheme F correspond to the compound numbers in Examples 1 and 2. Example 3 was prepared using the method of Examples 1 and 2 with the specific change as stated, and in the general manner described in Scheme A.

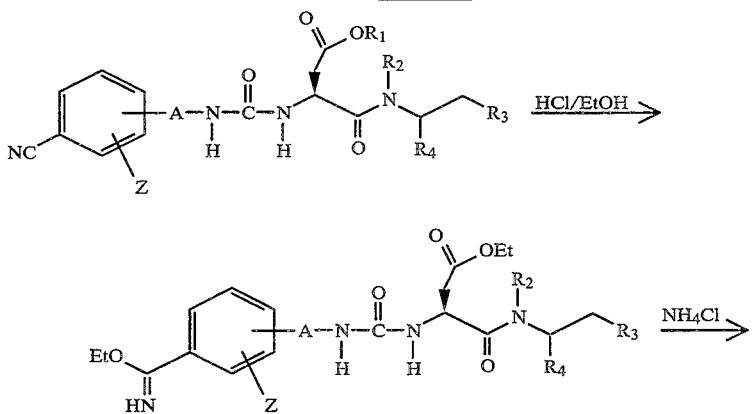

Scheme A

Scheme A
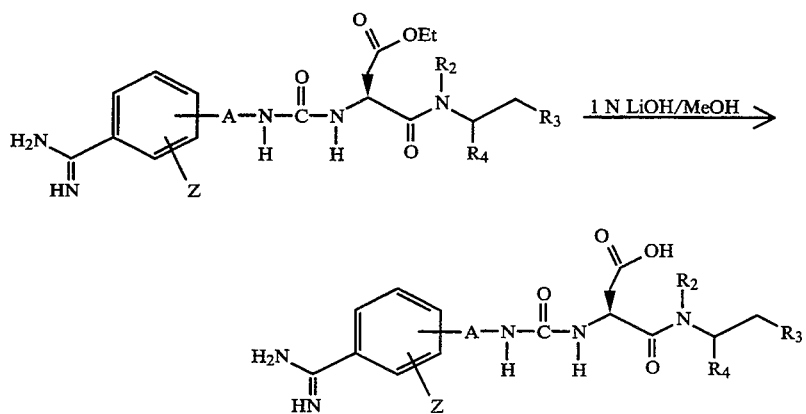
Scheme B
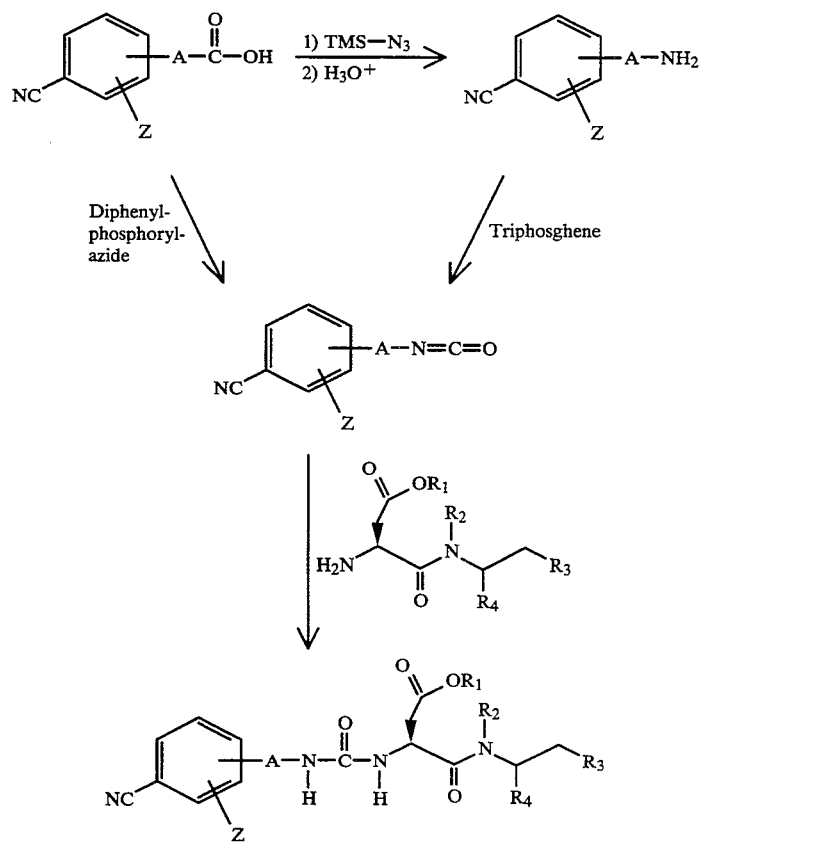
SCHEME C
Method 1
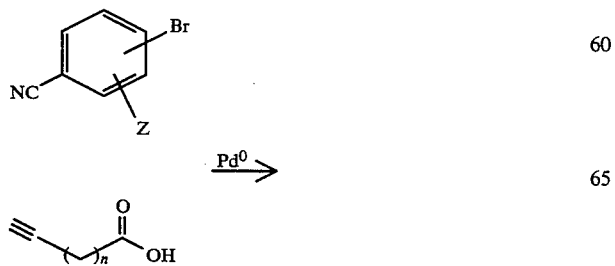
-continued
SCHEME C
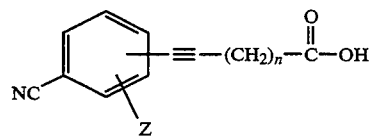
Method 2

11
-continued
SCHEME C
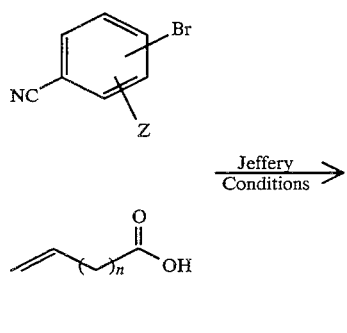
12
-continued
SCHEME C
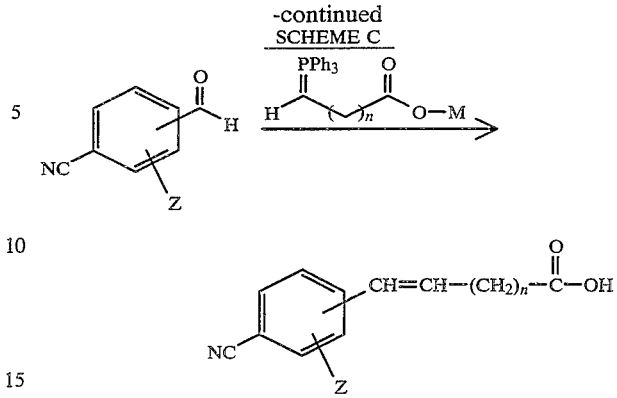
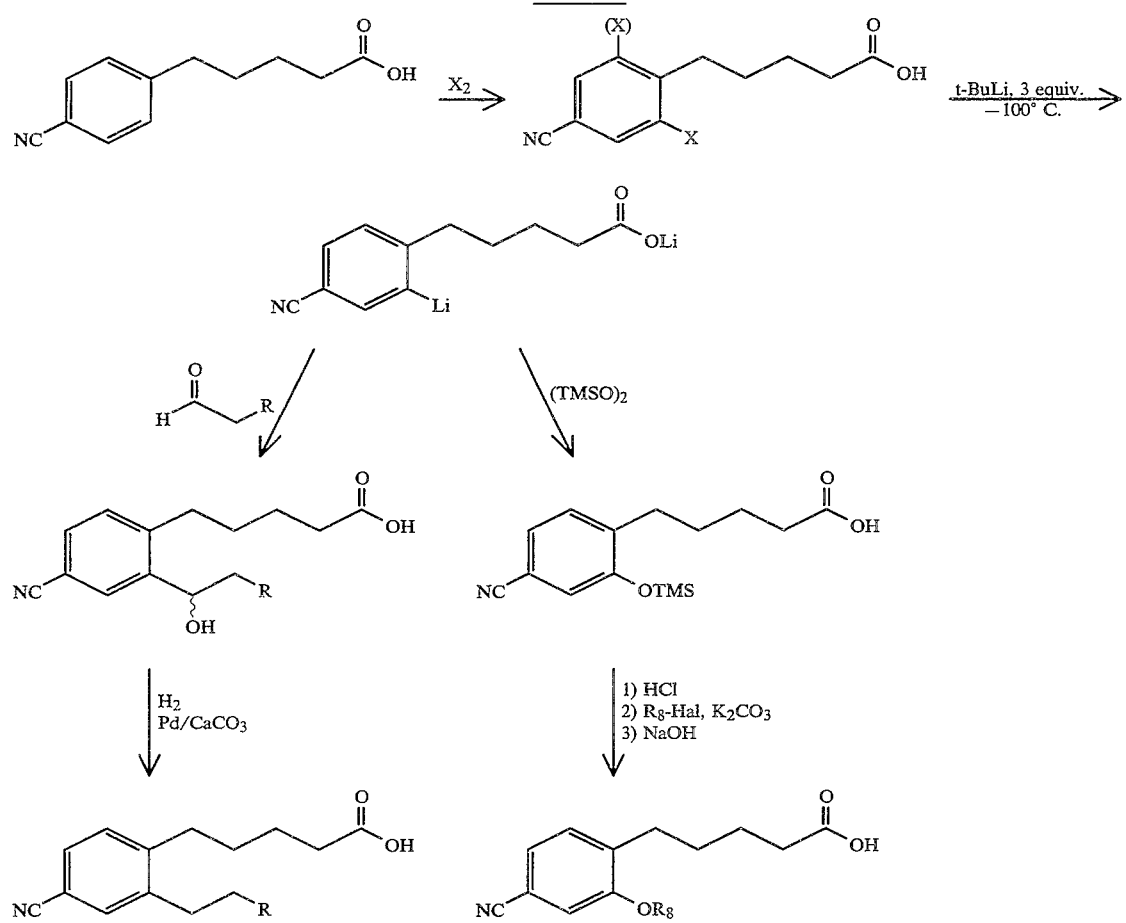
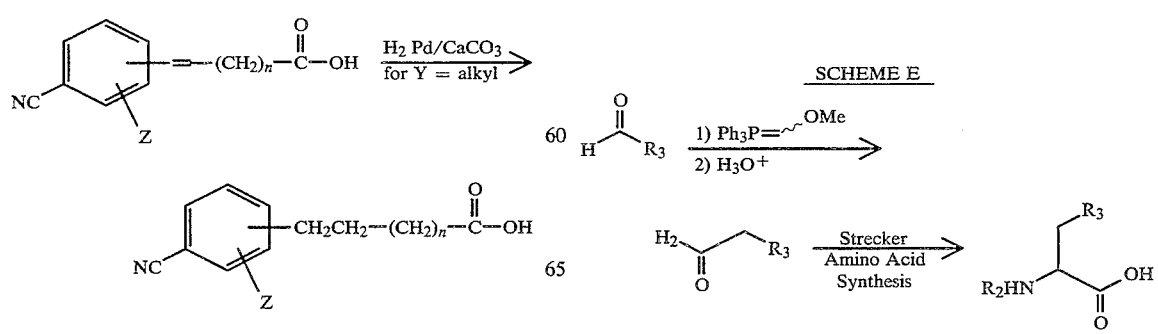
Method 3

Scheme F

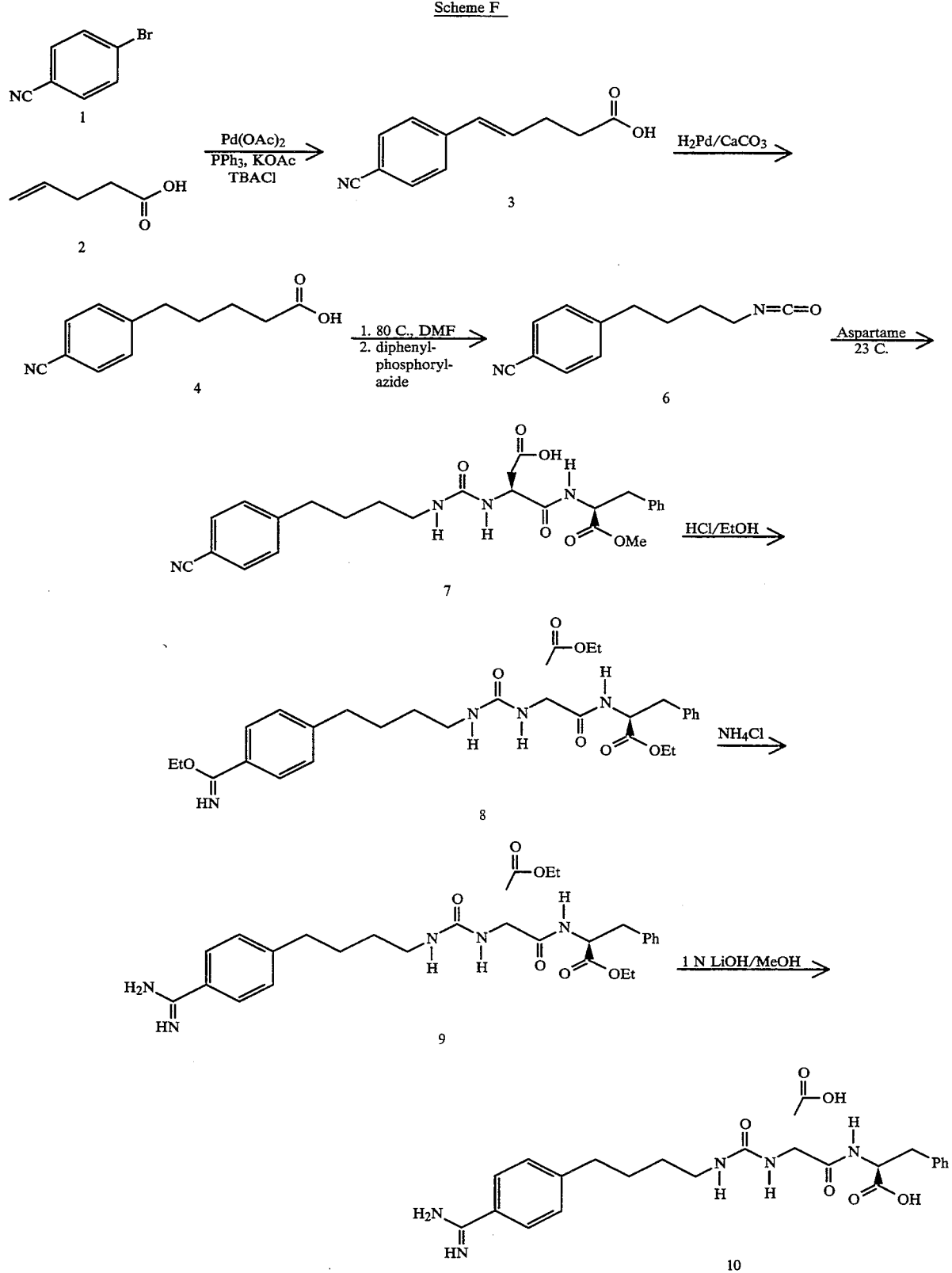

Contemplated equivalents of the platelet aggregation inhibitors, derivatives and intermediates of the formulas set forth above include compounds having the same general properties, wherein one or more of the various R groups are simple variations of the substituents as defined herein, e.g., wherein R is a higher alkyl group than that indicated. In addition, where a substituent can be a hydrogen, a substituent other than hydrogen can be introduced at that position, e.g., a hydrocarbon radical or a halogen, hydroxy, amino and the like, as long as the overall activity and/or synthesis procedure is not affected.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional.

The following examples are provided to illustrate the present invention and are not intended to limit the scope thereof. Those skilled in the art will readily understand that known variations of the conditions and processes of the following preparative procedures can be used to prepare the compounds of the present invention.

EXAMPLE 1

Preparation of N-[N-[[[4-[4-(aminoiminomethyl)phenyl]butyl]amino]carbonyl]-L-α-aspartyl]-L-phenylalanine, diethyl ester

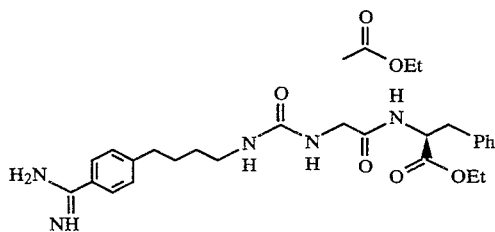

Section A.

5-(p-Cyanophenyl)-4-pentenoic acid (3)

Tetrabutylammonium chloride (hydrate, 17.8 g) was dried by azeotroping with benzene (250 mL round bottom flask equipped with a Dean-Stark apparatus). The benzene was removed in vacuo affording anhydrous tetrabutylammonium chloride (17.0 g, 61.2 mmol). To this flask under argon were added triphenylphosphine (820 mg, 3.13 mmol), palladium acetate (703 mg, 3.13 mmol), 4-bromobenzonitrile (16.9 g, 92.8 mmol), potassium acetate (36.8 g, 375 mmol) and 100 mL of degassed anhydrous dimethylformamide (degassed by bubbling argon through for 10 min, dried over molecular sieves). A solution of 4-pentenoic acid (6.27 g, 62.6 mmol) and degassed anhydrous DMF (35 mL) was then added to the rapidly stirring reaction mixture at 23° C. After 21 hours at 23° C., the reaction mixture was poured slowly into a sodium carbonate solution (3%, 400 mL) and extracted with ethyl acetate (500 mL). The aqueous layer was treated with decolorizing carbon, and filtered. Then, the aqueous layer was acidified to a pH of 2 with 10% HCl which afforded a white solid (6.82 g, 54%): m.p. 150°–167° C.

The above procedure affords (3) in sufficient purity to take on to the next step without complications. An analytical sample was obtained by submitting the sample to further purification by flash chromatography (ethyl acetate:methylene chloride:acetic acid, 1:4:0.05) and recrystallization from ethyl acetate (2 times): m.p. 154°–156° C.

Anal. Calcd. for $C_{12}H_{11}NO_2$: C, 71.63; H, 5.51; N, 6.96.

Found: C, 71.50; H, 5.54; N, 6.80.

Section B 5-(p-Cyanophenyl) pentanoic acid (4)

A solution of 1.47 g (7.32 mmol) of (3) in 90 mL of methanol was hydrogenated over 200 mg of 5% Pd/CaCO₃ at 5 psi hydrogen over a 1.2 hour period. After removing the catalyst by filtration and evaporation of the solvent in vacuo, the residue was triturated with ether followed by hexane which afforded a white solid: m.p. 101°–102° C.

Anal. Calcd. for $C_{12}H_{13}NO_2$: C, 70.92; H, 6.45; N, 6.89.

Found: C, 70.71; H, 6.56; N, 6.87.

Section C.

N-[N-[[[4-(4-cyanophenyl)butyl]aminocarbonyl]-L-α-aspartyl(O-methyl)]-L-phenylalanine 5-(4-cyanophenyl)pentanoic acid (1.01 g; 5 mmol) was dissolved in DMF (30 ml). Diphenylphosphorylazide (1.4 ml; 6 mmol) and N,N-diisopropylethylamine (1.7 ml; 10 mmol) were added slowly with stirring and the solution was heated up to 90° C. After 1 hour, additional diphenylphosphorylazide (0.25 ml) and N,N-diisopropyl-ethylamine (0.5 ml) were added and the reaction continued until the 5-(4-cyanophenylpentanoic acid disappeared on HPLC. The solution was cooled and Asp-Phe-OMe (1.76 g; 6 mmol) dissolved in DMF (10 ml) was added. The mixture was stirred at room temperature for another 3 hours and taken down to dryness on rotavapor to afford crude 7. The oil residue was used without any further purification (FAB-MS: MH+ =495).

Section D

N-[N-[[[4-[4-(aminoiminomethyl)phenyl]butyl]amino]carbonyl]-L-α-aspartyl]-L-phenylalanine, diethyl ester N-[N-[[[4-(4-cyanophenyl)butyl]amino]carbonyl]-L-α-aspartyl(O-methyl)]-L-phenylalanine was treated with HCl gas/ethanol (100 ml) in an ice bath for 1 hour. The reaction mixture was then stirred at room temperature over night. The solvent was removed on rotavapor and the residue was dissolved in ethanol (50 ml). Ammonium chloride (0.5 g) and ammonium hydroxide (3 ml in 10 ml H₂O) were added with vigorous stirring. The reaction mixture was gently refluxed overnight and taken down to dryness on rotavapor. The residue was purified on a HPLC Column as described above. A linear gradient of 10 to 40% acetonitrile/water/0.5% TFA over 30 min. and 40 to 60% acetonitrile/water/0.5% TFA over 5 min. was used. The desired peak was collected and lyophilized to yield 100 mg of 9 as a white solid (FAB-MS; MH+ =554).

EXAMPLE 2

N-[N-[[[4-[4-(aminoiminomethyl)phenyl]butyl]amino]-
carbonyl]-L-α-aspartyl]-L-phenylalanine

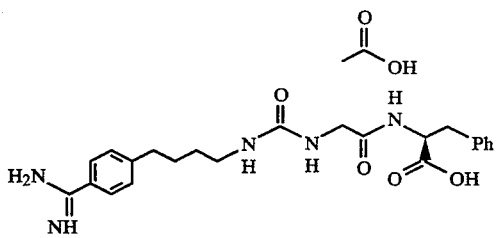

N-[[[4-[4-(aminoiminomethyl)phenyl]butyl]amino]-
carbonyl]-L-α-aspartyl]-L-phenylalanine, diethyl ester
(100 mg; 1.8 mmol), methanol (25 ml and 1N LiOH (25
ml) were stirred for 2 hours. Methanol was then removed on a rotary evaporator. The residue was dissolved in 20% acetic acid and purified by HPLC. A gradient of 10 to 40% acetonitrile/water/0.05% TFA over minutes was used. The desired peak was collected and lyophilized to yield 10 as a white solid (60 mg).

Fast Atom Bombardment Mass Spectrometry (MH+) 498

Anal. Calcd. for $C_{25}H_{31}N_5O_6$ plus $CF_3CO_2H$ and $H_2O$:

C,51.51; H,5.40; N,11.12. Found: C,51.40; H,4.84; N,10.98.

EXAMPLE 3

Preparation of N-[N-[[[4-[4-(amino
iminomethyl)phenyl]butyl]amino]carbonyl]-L-α-spartyl]-L-tryptophane

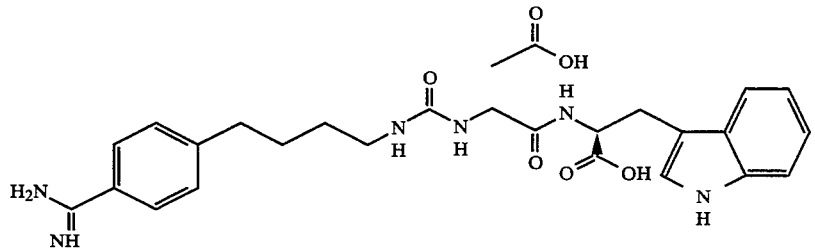

The title compound was prepared in the manner of Example 1 with the following substitution: L-α-aspartyl-L-tryptophane was substituted for L-α-aspartyl-L-phenylalanine in Section C. Fast Atom Bombardment Mass Spectrometry (MH+)=537.

EXAMPLE 4

Preparation of 4-(p-cyanophenyl)butylamine

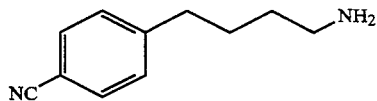

Oxalyl chloride (43.0 mL, 0.492 mol) was added dropwise to a suspension of 5-(p-cyanophenyl)pentanoic acid in 100 mL of dry 1,2-dichloroethane at 23° C. under a nitrogen atmosphere. After 5 min, 50 mL of DMF was added. After 30 min, the reaction was concentrated in vacuo. The residue was dissolved in anhydrous THF (150 mL) under a nitrogen atmosphere. Azidotrimethylsilane (14.6 mL, 0.110 mL) was added dropwise at 23° C. After 5 min, the reaction was warmed to achieve reflux for 1 hour. The reaction was cooled to 10° C. and concentrated HCl (20 mL) was added over 1 min. The cooling bath was removed and stirring was continued for 15 min. The reaction was concentrated in vacuo and the residue was partitioned between ethyl acetate (200 mL) and water (200 mL). The aqueous layer was made basic with 1N NaOH (250 mL) and extracted with ethyl acetate (2×200 mL). The organic layer was washed with water (100 mL) followed by brine (100 mL), and dried (Na2SO4). After concentration in vacuo, the residue was diluted with ethyl acetate; methanol (150 mL:5 mL) and treated with anhydrous HCl in dioxane (6.9N) at 0° C. The resultant precipitate was filtered, washed with ethyl acetate then ether. The solid was dried (atmospheric pressure; 55° C.) to afford 14.3 g: m.p. 155°-160° C.

Anal. Calcd. for $C_{11}H_{15}N_2Cl$: C,62.70; H,7.18; N,13.30.

Found: C,62.76; H,7.35; N,13.34.

EXAMPLE 5

Preparation of 4-[4-cyanophenyl)]butylisocyanate

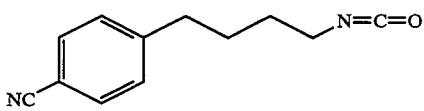

A solution of amine hydrochloride 5 (1.00 g, 4.74 mmol), triphosghene (0.469 g, 1.58 mmol), triethylamine (1.27 g, 12.6 mmol), and dioxane (20 mL) was warmed to 70° C. for 2 hours under an argon atmosphere. After cooling to 23° C., the reaction mixture was diluted with ethyl acetate (80 mL), filtered, and concentrated under a stream of nitrogen in the hood to afford the intermediate isocyanate.

EXAMPLE 6

Preparation of 5-(p-cyanophenyl)-4-pentynoic acid

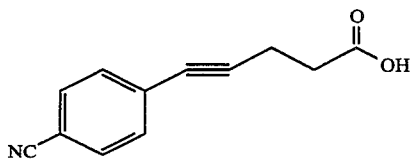

A solution of 4-pentynoic acid (2.15 g, 22 mmol), 4-bromobenzonitrile (3.64 g, 20 mmol), and piperidine (40 mL) was degassed by bubbling nitrogen through the solution for 5 min. prior to the addition of tetrakis(triphenylphosphine)palladium(0) (240 mg, 0.2 mmol). The reaction vial was sealed and warmed to 80° C. for 1.5 hours. After cooling to 23° C., the reaction mixture was diluted with ethyl acetate (200 mL), filtered, and concentrated in vacuo. The residue was diluted with ethyl acetate (300 mL), washed with 5% HCl (2×100 mL), washed with water (1×100 mL), and extracted with 3% sodium carbonate (2×200 mL). The basic aqueous layer was treated with decolorizing carbon, filtered, and acidified to pH=2. The resultant solid was filtered, washed with water, dried, and purified by flash chromatography (gradient ethyl acetate:methylene chloride:acetic acid 1:9:0.005) and fractional recrystallization (methylene chloride-ether) to afford 5-(p-cyanophenyl)-4-pentynoic acid as a white solid: m.p. 149°–152° C.

Anal. Calcd. for $C_{12}H_9NO_2$: C, 72.35; H, 4.55; N, 7.03.

Found: C, 72.05; H, 4.57; N, 6.94.

EXAMPLE 7

Preparation of N-[N-[[[4-[4-(amino iminomethyl)phenyl]-4-butynyl]amino]carbonyl]-L-α-spartyl]-L-phenylalanine

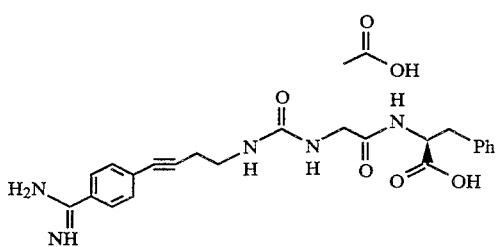

The title compound can be prepared in the manner of Example 1 with the following modification: the 5-(p-cyanophenyl)-4-pentynoic acid is substituted for 5-(p-cyanophenyl)pentanoic acid in Section C of Example 1. The product is purified by reverse phase HPLC using the conditions of Example 1 to afford the title compound. The product is verified by C NMR and Chemical Ionization Mass Spectrometry.

EXAMPLE 8

Preparation of N-[N-[[[4-[4-(aminoiminomethyl)phenyl]-4-butenyl-]amino]carbonyl]-L-α-aspartyl]-L-phenylalanine

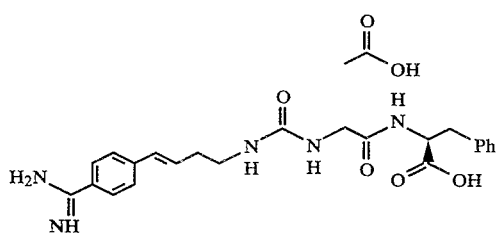

The title compound can be prepared in the manner of Example 1, but the reduction step is omitted (Section B). The product is purified by reverse phase HPLC using the conditions of Example 1 to afford the title compound. The product is verified by C NMR and Chemical Ionization Mass Spectrometry.

EXAMPLE 9

Preparation of 3S β-[[[[4-[4-(aminoiminomethyl)phenyl]butyl]amino]carbonyl]amino]-4-[(2-carboxyethyl)(2-methylpropyl)amino]-4-oxobutanoic acid

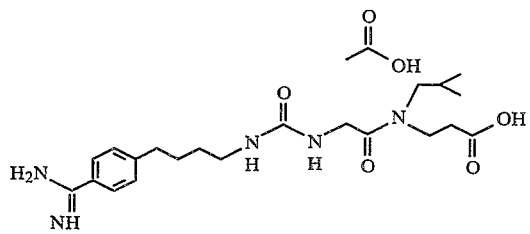

The title compound can be prepared substituting 3S-amino-4-[(2-carboxyethyl)(2-methylpropyl)amino]-4-oxobutanoic acid for aspartame in Section C of Example 1. The product is purified by reverse phase HPLC using the conditions of Example 1 to afford the title compound. The product is verified by C NMR and Chemical Ionization Mass Spectrometry.

EXAMPLE 10

Preparation of N-[N-[[[4-[4-(aminoiminomethyl)phenyl]butyl]amino]-carbonyl]-L-α-aspartyl]-N-methyl-L-phenylalanine

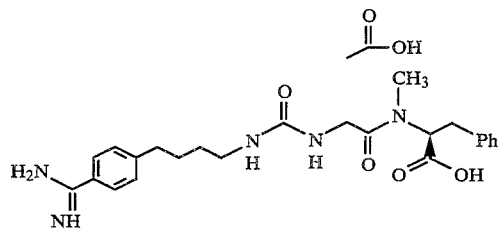

The title compound can be prepared substituting L-α-aspartyl-N-methyl-L-phenylalanine for aspartame in Section C of Example 1. The product is purified by reverse phase HPLC using the conditions of Example 1 to afford the title compound. The product is verified by C NMR and Chemical Ionization Mass Spectrometry.

EXAMPLE 11

Preparation of

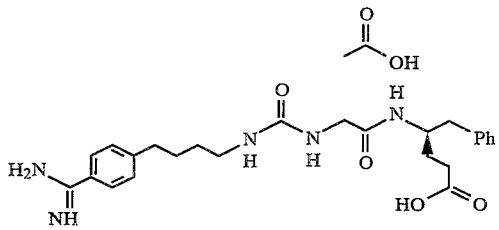

The title compound can be prepared substituting R-3-[[carboxy-1-oxopropyl]amino]-5-phenylpentanoic acid for aspartame in Section C of Example 1. The product is purified by reverse phase HPLC using the conditions of Example 1 to afford the title compound. The product is verified by C NMR and Chemical Ionization Mass Spectrometry.

The platelet-binding inhibitor activity of the compounds of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×$10^8$ platelets per ml. 400 µl of the PRP preparation and 50 µl of the compound to be tested or saline were preincubated for 1 minute at 37° C. in a BioData aggregometer (BioData, Horsham, Pa.). 50 µl of adenosine 5′-diphosphate (ADP) (50 µm final concentration) was added to the cuvettes and the aggregation was monitored for 1 minute. All compounds are tested in duplicate. Results are calculated as follows:

Percent of control=[(maximal OD minus initial OD of compound) divided by (maximal OD minus initial OD of control saline)]×100. The % inhibition=100 (percent of control).

The assay results for the compounds of Examples 2 and 3 and their median inhibitory concentrations ($IC_{50}$) are recorded in Table I. $IC_{50}$'s (if a compound showed 50% inhibition) were calculated by linear regression of the dose response curve.

TABLE I

| Example | Dog PRP $IC_{50}$ Micro M |
|---|---|
| 2 | 0.76 |
| 3 | 0.20 |

What is claimed is:

1. A compound of the formula

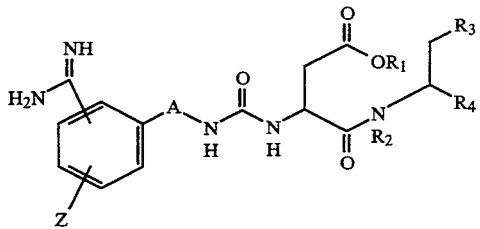

or a pharmaceutically acceptable salt thereof wherein Z is selected from the group consisting of H, halogen, hydroxy, alkoxy of from one to six carbon atoms and alkyl of from one to six carbon atoms;

wherein A is selected from the group consisting of alkyl of one to six carbon atoms, alkenyl of two to six carbon atoms and alkynyl of two to six carbon atoms;

wherein $R_1$ is selected from the group consisting of H, alkyl of one to six carbon atoms, aralkyl wherein the alkyl is of one to six carbon atoms and alkanoyloxyalkyl wherein the alkyl is of one to six carbon atoms; and wherein $R_2$ is selected from the group consisting of H, alkyl of one to six carbon atoms, and aralkyl wherein the alkyl is of one to six carbon atoms optionally substituted with hydroxy and methoxy;

wherein $R^3$ is selected from the group consisting of alkyl of one to six carbon atoms, indolyl, pyridyl, benzothiophenyl, phenyl, benzofuranyl and furanyl all optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein $R_6$ is alkyl of one to six carbon atoms, alkoxycarbonyloxy wherein the alkoxy is from one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;

wherein $R^4$ is selected from the consisting of H,—COOR$_5$ and —(CH$_2$)$_m$COOR$_5$;

wherein m is an integer from 1 to 6; and wherein $R_5$ is selected from the group consisting of H, alkyl of one to six carbon atoms and aralkyl wherein the alkyl is of one to six carbon atoms.

2. A compound according to claim 1 wherein
Z is hydrogen;
A is alkyl of one to six carbon atoms;
$R_1$ is selected from the group consisting of hydrogen and alkyl of one to six carbon atoms;
$R_2$ is selected from the group consisting of hydrogen, alkyl of one to six carbon atoms, and aralkyl wherein the alkyl is of one to six carbon atoms optionally substituted by hydroxy or methoxy;
wherein $R^3$ is indolyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein $R_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;
wherein $R^4$ is selected from the consisting of H,—COOR$_5$ and —(CH$_2$)$_m$COOR$_5$;
wherein m is an integer from 1 to 6; and
wherein $R_5$ is selected from the group consisting of H, alkyl of one to six carbon atoms and aralkyl wherein the alkyl is of one to six carbon atoms.

3. A compound according to claim 2 which is N-[N-[[[4-[4(aminoiminomethyl)phenyl]butyl]amino]carbonyl]-L-α-aspartyl]-L-tryptophane.

4. A compound according to claim 1 wherein
Z is hydrogen;
A is alkyl of one to six carbon atoms;

$R_1$ is selected from the group consisting of hydrogen and alkyl of one to six carbon atoms;

$R_2$ is selected from the group consisting of hydrogen, alkyl of one to six carbon atoms, and aralkyl wherein the alkyl is of one to six carbon atoms optionally substituted by hydroxy or methoxy;

wherein $R^3$ is phenyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein R$_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;

wherein $R^4$ is selected from the consisting of H,—COOR$_5$ and —(CH$_2$)$_m$COOR$_5$;

wherein m is an integer from 1 to 6; and wherein $R_5$ is selected from the group consisting of H, alkyl of one to six carbon atoms and aralkyl wherein the alkyl is of one to six carbon atoms.

5. A compound according to claim 4 which is N-[N-[[[4-[4-(aminoiminomethyl)phenyl] butyl]amino]carbonyl]-L-α-aspartyl]-L-phenylalanine, diethyl ester.

6. A compound according to claim 4 which is N-[N-[[[4-[4-(aminoiminomethyl)phenyl]butyl]amino]carbonyl]-L-α-aspartyl]-L-phenylalanine.

7. A pharmaceutical composition comprising a compound of the formula

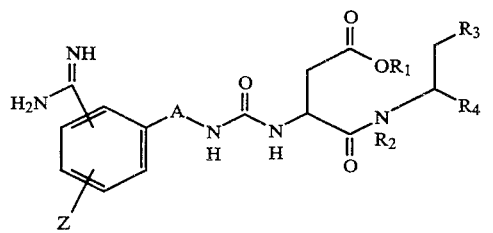

or a pharmaceutically acceptable salt thereof wherein Z is selected from the group consisting of H, halogen, hydroxy, alkoxy of from one to six carbon atoms and alkyl of from one to six carbon atoms;

wherein A is selected from the group consisting of alkyl of one to six carbon atoms, alkenyl of two to six carbon atoms and alkynyl of two to six carbon atoms;

wherein $R_1$ is selected from the group consisting of H, alkyl of from one to six carbon atoms, aralkyl wherein the alkyl is of one to six carbon atoms and alkanoyloxyalkyl wherein the alkyl is of one to six carbon atoms; and wherein $R_2$ is selected from the group consisting of H, alkyl of from one to six carbon atoms, and aralkyl wherein the alkyl is of one to six carbon atoms optionally substituted by hydroxy or methoxy;

wherein $R^3$ is selected from the group consisting of alkyl wherein the alkyl is of one to six carbon atoms, indolyl, pyridyl, benzothiophenyl, benzofuranyl and furanyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein R$_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;

wherein $R^4$ is selected from the consisting of H,—COOR$_5$ and —(CH$_2$)$_m$COOR$_5$;

wherein m is an integer from 1 to 6; and wherein $R_5$ is selected from the group consisting of H, alkyl of one to six carbon atoms and aralkyl wherein the alkyl is of one to six carbon atoms and a pharmaceutically acceptable carrier.

8. A pharmaceutical composition according to claim 7 wherein

Z is hydrogen;

A is alkyl of one to six carbon atoms;

$R_1$ is selected from the group consisting of hydrogen and alkyl of one to six carbon atoms; and $R_2$ is selected from the group consisting of hydrogen, alkyl of one to six carbon atoms, and aralkyl wherein the alkyl is of one to six carbon atoms optionally substituted by hydroxy or methoxy;

wherein $R^3$ is indolyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein R$_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;

wherein $R^4$ is selected from the consisting of H,—COOR$_5$ and —(CH$_2$)$_m$COOR$_5$;

wherein m is an integer from 1 to 6; and wherein $R_5$ is selected from the group consisting of H, alkyl of one to six carbon atoms and aralkyl wherein the alkyl is of one to six carbon atoms.

9. A pharmaceutical composition according to claim 8 wherein the compound is N-[N-[[[4-[4-(aminoiminomethyl)phenyl]butyl]amino]carbonyl]-L-L-α-aspartyl]tryptophane.

10. A pharmaceutical composition according to claim 7 wherein Z is hydrogen;

A is alkyl of one to six carbon atoms;

$R_1$ is selected from the group consisting of hydrogen and alkyl of one to six carbon atoms;

$R_2$ is selected from the group consisting of hydrogen, alkyl of one to six carbon atoms, and aralkyl wherein the alkyl is of one to six carbon atoms optionally substituted by hydroxy or methoxy;

wherein $R^3$ is phenyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein R$_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;

wherein R$^4$ is selected from the consisting of H,—COOR$_5$ and —(CH$_2$)$_m$COOR$_5$;

wherein m is an integer from 1 to 6; and wherein R$_5$ is selected from the group consisting of H, alkyl of one to six carbon atoms and aralkyl wherein the alkyl is of one to six carbon atoms.

11. A pharmaceutical composition according to claim 10 wherein the compound is N-[N-[[[4-[4-(aminoiminomethyl)phenyl]butyl]amino]carbonyl]-L-α-aspartyl]-L-phenylalanine, diethyl ester.

12. A pharmaceutical composition according to claim 10 wherein the compound is N-[N-[[[4-[4-(aminoiminomethyl)phenyl]butyl]amino]carbonyl]-L-α-aspartyl]-L-phenylalanine.

13. A method of treating a mammal to inhibit platelet aggregation comprising administering a therapeutically effective amount of a compound of the formula

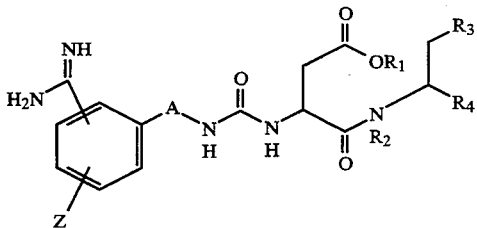

or a pharmaceutically acceptable salt thereof wherein Z is selected from the group consisting of H, halogen, hydroxy, alkoxy of from one to six carbon atoms and alkyl of from one to six carbon atoms;

wherein A is selected from the group consisting of alkyl of one to six carbon atoms, alkenyl of two to six carbon atoms and alkynyl of two to six carbon atoms;

wherein R$_1$ is selected from the group consisting of H, alkyl of from one to six carbon atoms, aralkyl wherein the alkyl is of one to six carbon atoms and alkanoyloxyalkyl wherein the alkyl is of one to six carbon atoms; and wherein R$_2$ is selected from the group consisting of H, alkyl of from one to six carbon atoms and aralkyl wherein the alkyl is of one to six carbon atoms optionally substituted by hydroxy or methoxy;

wherein R$^3$ is selected from the group consisting of alkyl wherein the alkyl is of one to six carbon atoms, indolyl, pyridyl, benzothiophenyl, benzofuranyl and furanyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein R$_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;

wherein R$^4$ is selected from the consisting of H,—COOR$_5$ and —(CH$_2$)$_m$COOR$_5$;

wherein m is an integer from 1 to 6; and wherein R$_5$ is selected from the group consisting of H, alkyl of one to six carbon atoms and aralkyl wherein the alkyl is of one to six carbon atoms.

14. A method according to claim 13 wherein

Z is hydrogen;

A is alkyl of one to six carbon atoms;

R$_1$ is selected from the group consisting of hydrogen and alkyl of one to six carbon atoms; and R$_2$ is selected from the group consisting of hydrogen, alkyl of one to six carbon atoms, and aralkyl wherein the alkyl is of one to six carbon atoms optionally substituted by hydroxy or methoxy;

wherein R$^3$ is indolyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein R$_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;

wherein R$^4$ is selected from the consisting of H,—COOR$_5$ and —(CH$_2$)$_m$COOR$_5$;

wherein m is an integer from 1 to 6; and wherein R$_5$ is selected from the group consisting of H, alkyl of one to six carbon atoms and aralkyl wherein the alkyl is of one to six carbon atoms.

15. A method according to claim 14 wherein the compound is N-[N-[[[4-[4-(aminoiminomethyl)phenyl]-butyl]-amino]carbonyl]-L-α-aspartyl]-L-tryptophane.

16. A method according to claim 13 wherein

Z is hydrogen;

A is alkyl of one to six carbon atoms;

R$_1$ is selected from the group consisting of hydrogen and alkyl of one to six carbon atoms;

R$_2$ is selected from the group consisting of hydrogen, alkyl of one to six carbon atoms, and aralkyl wherein the alkyl is of one to six carbon atoms optionally substituted by hydroxy or methoxy;

wherein R$^3$ is phenyl optionally substituted by a radical selected from the group consisting of halogen, alkyl of one to six carbon atoms, alkoxy of one to six carbon atoms, —COOR wherein R is hydrogen or alkyl of one to six carbon atoms, nitro, cyano, azido, ureido, —NH—CO—NHR$_6$ wherein R$_6$ is alkyl of one to six carbon atoms, alkoxycarbonyloxy wherein the alkoxy is of one to six carbon atoms, hydroxyl, alkylamino wherein the alkyl is of one to six carbon atoms, alkoxycarbonyl wherein the alkoxy is of one to six carbon atoms, trialkylsilyl wherein the alkyl is of one to six carbon atoms, alkoxyimino wherein the alkoxy is of one to six carbon atoms, alkylsulfonyl wherein the alkyl is of one to six carbon atoms, phenylsulfonyl and amino;
wherein $R^4$ is selected from the consisting of H, —COOR$_5$ and —(CH$_2$)$_m$COOR$_5$;
wherein m is an integer from 1 to 6; and
wherein R$_5$ is selected from the group consisting of H, alkyl of one to six carbon atoms and aralkyl wherein the alkyl is of one to six carbon atoms.

17. A method according to claim 16 wherein the compound is N-[N-[[[4-[4-(aminoiminomethyl)phenyl]-butyl]-amino]carbonyl]-L-α-aspartyl]-L-phenylalanine, diethyl ester.

18. A method according to claim 16 wherein the compound i s N-[N-[[[4-[4-(aminoiminomethyl)phenyl]-butyl]-amino]carbonyl]-L-α-aspartyl]-L-phenylalanine.

* * * * *

UNITED STATES PATENT AND TRADEMARK OFFICE
CERTIFICATE OF CORRECTION

PATENT NO. : 5,354,738
DATED : October 11, 1994
INVENTOR(S) : Tjoeng, et al.

It is certified that error appears in the above-indentified patent and that said Letters Patent is hereby corrected as shown below:

Column 8, line 35, reading "*Tetrahedrron*" should read -- *Tetrahedron* --.

Column 11, line 25 -- Scheme D has been inserted into the middle of Scheme C, please re-position Scheme D to come after Scheme C --.

Column 12, line 63, that part of Scheme E reading

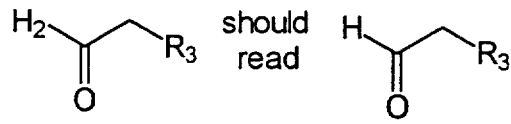

At Column 14, lines 30 and 40 and column 15, line 30, all occurrences of that part of the formula reading

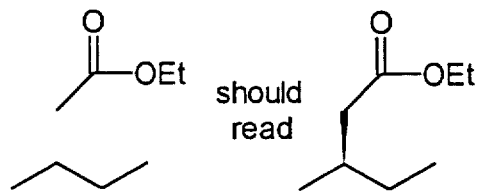

UNITED STATES PATENT AND TRADEMARK OFFICE
CERTIFICATE OF CORRECTION

PATENT NO. : 5,354,738
DATED : October 11, 1994
INVENTOR(S) : Tjoeng, et al.

It is certified that error appears in the above-indentified patent and that said Letters Patent is hereby corrected as shown below:

At Column 14, line 55, column 17, line 8, column 17, line 40, column 19, lines 28 and 55, column 20, lines 10, 35 and 55, all occurrences of that part of the formula reading

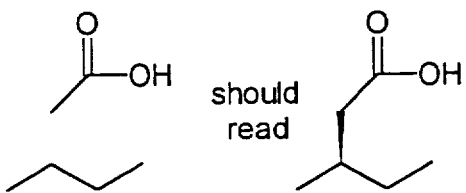

Column 17, line 23, reading "over minutes" should read -- over 30 minutes --.

Column 17, line 35, reading "-α-spartyl" should read -- -α-aspartyl --.

Column 19, line 24, reading "-α-spartyl" should read -- -α-aspartyl --.

UNITED STATES PATENT AND TRADEMARK OFFICE
CERTIFICATE OF CORRECTION

PATENT NO. : 5,354,738
DATED : October 11, 1994
INVENTOR(S) : Tjoeng, et al.

It is certified that error appears in the above-indentified patent and that said Letters Patent is hereby corrected as shown below:

At Column 22, lines 26 and 57, column 23, line 22, column 24, lines 13 and 46, column 25, line 13, column 26, lines 7 and 38 and column 27, line 3, all occurrences reading "the consisting" should read -- the group consisting --.

Signed and Sealed this

Third Day of October, 1995

Attest:

BRUCE LEHMAN

Attesting Officer     Commissioner of Patents and Trademarks